United States Patent [19]

Konishi et al.

[11] Patent Number: 5,560,935
[45] Date of Patent: Oct. 1, 1996

[54] PHYSIOLOGICALLY ACTIVE SUBSTANCES EXTRACTED FROM ACTIVATED TISSUES

[75] Inventors: Jin-emon Konishi, Musashino; Giichi Hamada, Nishinomiya, both of Japan

[73] Assignee: Nippon Zoki Pharmaceutical Co., Ltd., Osaka, Japan

[21] Appl. No.: 312,640

[22] Filed: Sep. 27, 1994

[30] Foreign Application Priority Data

Sep. 28, 1993 [JP] Japan ................. 5-265589

[51] Int. Cl.$^6$ .................. A61K 31/275; A61K 31/215; A61K 31/225; A61K 31/19
[52] U.S. Cl. .......... 424/520; 424/529; 424/548; 424/557; 424/558; 424/559; 424/562; 424/563; 424/570; 424/683; 424/684; 424/704; 424/723; 514/769; 514/825; 514/886
[58] Field of Search ................. 424/520, 723, 424/704, 684, 683, 529, 548, 558, 559, 557, 562, 563, 570; 514/769, 825, 886

[56] References Cited

U.S. PATENT DOCUMENTS

| | | | |
|---|---|---|---|
| 3,959,566 | 5/1976 | Pangonis | 428/446 |
| 4,036,787 | 7/1977 | Blount | 528/405 |
| 4,039,474 | 8/1977 | Feistel et al. | 502/8 |
| 4,056,937 | 11/1977 | Suzuki | 61/36 B |
| 4,089,883 | 5/1978 | Blount | 536/107 |
| 4,138,421 | 2/1979 | Blount | 556/443 |
| 4,863,518 | 9/1989 | Blount | 106/634 |
| 4,985,254 | 1/1991 | Konishi et al. | 424/520 |
| 4,985,354 | 1/1991 | Toyomaki et al. | 435/13 |
| 5,013,558 | 5/1991 | Konishi | 424/520 |
| 5,057,324 | 10/1991 | Shibayama et al. | 424/520 |
| 5,127,994 | 7/1992 | Johansson | 162/168.3 |
| 5,227,089 | 7/1993 | Hasegawa et al. | 252/181 |

FOREIGN PATENT DOCUMENTS

| | | |
|---|---|---|
| 0341209A2 | 11/1989 | European Pat. Off. . |
| 53-101515 | 9/1978 | Japan . |
| 57-77697 | 5/1982 | Japan . |
| 58-35117 | 3/1983 | Japan . |
| 697351 | 9/1953 | United Kingdom . |

OTHER PUBLICATIONS

Yokoi, et al., "Effect of Degree of Polymerization of Silicic Acid on the Gastrointestinal Absorption of Silicate in Rats", *Chem. Pharm. Bull.*, vol. 27, No. 8, 1979, pp. 1733–1739.

Derwent Publications Ltd., London, GB; AN 82–10241J, "Drug For Cultivated Fish", & JP A57183720 (Mitani J.), 12 Nov. 1982, abstract.

"Remedy For Burn", *Patent Abstracts of Japan*, vol. 7, No. 255 (C–189), 6 Oct. 1983, & JPA58121217 (Kagitani Takeo) 19 Jul. 1983, abstract.

"Drug For Food Poisoning", *Patent Abstracts of Japan*, vol. 11, No. 371 (C–462), 3 Dec. 1987 & JPA62145022 (Sofuto Shirika) 29 Jun. 1987, abstract.

"Adsorbent For Peroxylipid", *Patent Abstracts of Japan*, vol. 15, No. 474 (C–890), 3 Dec. 1991 & JPA3204803 (Shiseido Co. Ltd.) 6 Sep. 1991, abstract.

The Merck Index, 9th ed, 1976. No. 7u56, 8443, 8233–8243 & 5514–5515.

*Primary Examiner*—John W. Rollins
*Attorney, Agent, or Firm*—Fisher, Christen & Sabol

[57] ABSTRACT

The present invention provides a physiologically active substance which inhibits plasma kallikrein production, improves peripheral blood flow, and exhibits analgesic, antiinflammatory and antiallergic action. The physiologically active substance of the present invention is prepared by activating various animals or animal tissues by means of inoculation with virus or tumor cells which act as a stressor, and then extracting the effective factor from the activated tissues. The substance exhibits a pharmacological action of inhibiting activity for production of plasma kallikrein and recovering and normalizing abnormal functions which are associated with the diseased state. The physiologically active substance and pharmaceutical compositions of the present invention exhibit excellent regulating activity for biofunctions. They provide recovery and normalization of abnormal functions in living organisms in various diseased states. The compositions are useful as pharmaceuticals such as peripheral blood flow improving agents, analgesic agents, antiinflammatory agents and antiallergic agents. The physiologically active composition which is extracted from the activated tissue comprises an amorphous and hygroscopic powder containing 1–20 micrograms/mg of at least one silicon component calculated as silicon such as a water-soluble silicic acid, water-soluble silicate, a polymer of a water-soluble silicic acid, and a polymer of a water-soluble silicate. The powder is soluble in water, methanol and ethanol and is insoluble in benzene and ether. The powder may have a pH of 6.0 to 8.3, and ultraviolet absorptions of $\lambda_{max}$=265–275 nm.

17 Claims, No Drawings

PHYSIOLOGICALLY ACTIVE SUBSTANCES EXTRACTED FROM ACTIVATED TISSUES

FIELD OF THE INVENTION

The present invention relates to physiologically active substances which are extracted from a tissue or cells activated by internal and external stressors, and to methods for producing the physiologically active substances. The present invention also relates to pharmaceutical compositions containing the physiologically active substances.

BACKGROUND OF THE INVENTION

Living organisms survive as an individual by adjusting and maintaining their physical and chemical states to and within certain stable physiological conditions corresponding to changes in internal and external circumstances. To maintain and adjust such homeostasis, the living organism always produces various substances in vivo. Upon invasion by viruses, bacteria, etc. and upon generation of tumor cells, the organism also produces certain substances in vivo which are resistant to such external and internal invasions. However, if the biofunctions are unbalanced for some reason and it becomes chronic, so-called morbidity results causing various diseases.

The ideal way of curing the disease is to activate and adjust the function of the organism to maintain homeostasis so that the abnormal imbalance of the disordered biofunction is restored to a normal state. It has been well known that the maintenance and the normalization of the biofunction are especially carried out by various receptors on cell surfaces and the ion channels such as sodium, potassium, calcium, etc.

It has been known that, upon growing older, the ability of DNA to recover against damage decreases in mammalian cells. It is also known that the production of free radicals in vivo promotes aging, collagen disease and generation of cancer. For example, collagen is a noncellular substance widely present in skin, blood vessels, cartilage, eye balls, kidneys, etc. Crosslinking of collagenous materials proceeds with advancing age whereby their elasticity decreases and they become hard. It has been well known that, in patients suffering from diabetes, an excessive crosslinking of the collagenons materials proceeds as a result of a continuing high sugar level in the blood. The crosslinking of the collagenous material may result in cataracts, atherosclerosis, renal diseases, peripheral nervous disorders, etc.

The present inventors have focused on the function of maintaining homeostasis of living organisms which adjusts to and recovers from strains in the nervous, immunological and endocrine systems. The strains are caused by a disorder of cell functions in vivo as a result of diseases and aging. The present inventors have conducted an extensive investigation to ascertain the substances which: 1) are produced at the resisting stage of organisms against internal and external stresses (i.e., at the activating stage of the living tissues), and 2) promote the natural curing ability of the organisms to participate in the normalization of the biofunctions.

A known mechanism for adjusting the complicated functions in vivo is an enzymatic system called the kallikrein-kinin system. With respect to this plasma kallikrein-kinin system, it is believed that a blood coagulation factor XII (a Hageman factor, abbreviated as FXII) is activated due to stimulation by a lesion or by an invasion to the tissues in vivo whereby a series of enzymatic reactions is induced. Thus, the activated blood coagulation factor XII (abbreviated as FXIIa) acts on the plasma prekallikrein which exists in the same plasma to convert it to a plasma kallikrein which is an enzyme in an activated form. Then, the plasma kallikrein acts on a high-molecular-weight kininogen (abbreviated as an HK) in the plasma to liberate bradykinin.

The bradykinin which is a product of the plasma kallikrein-kinin system exhibits various physiological activities such its dilation of peripheral blood vessels which lowers blood pressure, acceleration of permeation of blood vessels, contraction or relaxation of smooth muscle, induction of pain, generation of inflammation, migration of leucocytes, liberation of catecholamine from the adrenal cortex, etc. Bradykinin has also been known as a mediator for induction of pain, inflammation and allergic reactions. Accordingly, when an excessive liberation and production of bradykinin is inhibited, it is possible to relieve pain, inflammation, allergic syndromes, etc. and to make such unhealthy states normal.

As mentioned above, bradykinin is liberated or produced in the reaction of plasma kallikrein with the high-molecular-weight kininogen HK. Accordingly, substances which inhibit kallikrein production in the plasma kallikrein-kinin system and prevent excessive production of bradykinin may be useful as pharmaceuticals such as analgesics, antiinflammatory agents, antiallergic drugs, etc.

In the present invention physiologically active substances which possess biofunction-adjusting and maintenance properties are obtained by subjecting tissues to stress or activation and then recovering the active substances produced as a result of the induced stress or activation. The physiologically active substances of the present invention provide recovery from and normalizes abnormal functions of the diseased state. They inhibit production of plasma kallikrein. They improve peripheral blood flow and are useful as analgesics, antiinflammatory agents, antiallergic agents, and other pharmaceuticals.

SUMMARY OF THE INVENTION

The present invention provides novel physiologically active substances or compositions which exhibit biofunction-adjusting and maintenance properties for recovery from and normalization of abnormal functions associated with a diseased state. In embodiments of the present invention, various animals or animal tissues are inoculated with virus or tumor cells as a stressor to activate the tissues. The novel physiologically active substances of the present invention are extracted from the resulting stressed or activated tissues. The biofunction-adjusting and maintaining substances which are extracted exhibit an activity for inhibiting the production of plasma kallikrein. The extracted substances improve peripheral blood flow and exhibit analgesic, antiinflammatory, and antiallergic activity.

In accordance with the methods of the present invention the physiologically active substance may be obtained by grinding the stressed or activated tissues of the animal, admixing the ground activated tissues with a solvent for extraction of the substance, removing tissue residues from the resulting emulsified suspension, and then removing proteins. Then, the remainder of the emulsified suspension is subjected to adsorption with an adsorbent. The adsorbed substance may then be eluted, and the eluent can then be dried to obtain the physiologically active substance of the present invention.

The physiologically active substances obtained in the method of the present invention contain silicon in the form of water-soluble silicic acids, silicates, polymers of silicic acids or silicates, and mixtures thereof. The silicon component content (e.g. water-soluble silicic acids, silicates, and polymers thereof) may range from 1 to 20 micrograms per mg of the isolated dried, powdery product, calculated as silicon. The silicon component content preferably ranges from 1.5 to 15 micrograms/rag calculated as silicon. The pharmaceutical compositions of the present invention comprise a pharmaceutically effective amount of the physiologically active substance and may be used for the treatment or prevention of diseases, ailments or symptoms associated with allergies, inflammation, or pain. The pharmaceutical compositions may be produced in solid, semi-solid, liquid, or aerosol forms for oral or parenteral administration.

DETAILED DESCRIPTION OF THE INVENTION

The physiologically active, silicon containing substances of the present invention are obtained by stressing or activating tissues with one or more stressors so that the tissues generate substances for returning the tissues to their normal state. The stressed or activated tissues are then treated to extract, isolate, recover or remove the biofunction-adjusting and maintaining substances which are generated, released, or produced in response to the induced stress or activation. The physiologically active substances which are recovered from the stressed or activated tissues inhibit production of plasma kallikrein, improve peripheral blood flow, and exhibit excellent analgesic, antiinflammatory, and antiallergic activity.

The activated or stressed animal tissues which may be used in the present invention include cultured tissues, cultured cells or inflammatory tissues of human or animal origin which are infected with virus, or chorio-allantoic membranes of embryonated eggs infected with virus. Examples of the one or more viruses which may be used as a stressor for the activation of the animal tissues are vaccinia virus, cowpox virus, variola virus, ectromelia virus, simian pox virus and other orthopox viruses, Orf virus, paravaccinia virus, bovine nopplelike stomatitis virus and other parapoxviruses, sheep pox virus, goatpox virus, lumpy skin disease virus and other goatpox viruses, avian pox virus, hare fibroma virus and other avian pox viruses, rabbit myxoma virus, rabbit fibroma virus and other rabbit pox viruses as well as swine pox virus, Yava monkey tumor virus, Tara pox virus and other viruses belonging to the family poxvirus. Examples of the tumor cells which may be used as a stressor or activator are various tumor-cultured cell strains derived from human beings and animals and mixtures of different strains of tumor cells. Anything which can be inoculated into the animals and animal tissues to cause stress or activation may be used. The stressors may include combinations of viruses and tumor cells.

Exemplary of animals which may be used for preparing the activated tissues are domestic animals and fowls such as rabbits, cows, horses, sheep, goat, swines, chickens, etc. and mammals such as monkeys, rats, mice, guinea pigs, hamsters, etc. They may be selected depending upon the type of the stressors and the object or pharmaceutical effect desired. With respect to the cells which may be used for the culture, any cell will do provided the stressor used is able to grow there. Examples of cells which may be used for the culture are various tissues (e.g. human hemocytes and placemac) and the cells of various culturable tissues such as kidney, skin, lung, testis, muscle, adrenal gland, thyroid gland, brain, and nerve cells, hemocytes, etc. of the above-mentioned animals and embryos thereof.

The activated tissues or cells are aseptically collected, ground and made into an emulsified suspension by adding 1 to 5 times as much extracting solvent thereto. Examples of the extracting solvent applicable are distilled water, physiologically saline solution, weakly acidic to weakly basic buffers. etc. If necessary, stabilizers such as glycerol, antibacterial/antiseptic agents such as phenol, inorganic salts such as sodium chloride, potassium chloride, magnesium chloride, etc. may be added thereto in conventional amounts. At that time, the extraction can be facilitated by subjecting the admixture to treatment by means of freezing/melting, ultrasonic waves, cell membrane dissolving enzymes or surface-active agents.

The resulting milky extract is filtered or centrifuged to remove the tissue residue and then proteins are removed therefrom. Removal of the proteins can be carried out by known methods and treatments such as heating, ultrasonic waves, protein denaturing agents such as acids, bases, urea, guanidine, organic solvents, surface-active agents, etc., isoelectric precipitation, salting-out, and the like. Then the proteins separated out therefrom are filtered off by means of filtration using filter paper (cellulose, nitrocellulose, etc.), a glass filter, Celite, a Seitz filter, etc. as well as ultrafiltration, gel filtration, an ion exchange resin, centrifugation and the like.

The resulting extracted fraction is adjusted to an acidic pH, preferably to pH 3.5–5.5, by an acid such as hydrochloric acid, sulfuric acid, hydrobromic acid, etc. and adsorbed with an adsorbent. Examples of adsorbents which may be used are activated charcoal, kaolin, ion exchange resins, etc. The adsorbent may be added to the extract followed by stirring or the extract may be passed through a column filled with the adsorbent whereby the effective component can be adsorbed.

In eluting the substance of the present invention from the adsorbent, an extracting solvent is added. Exemplary solvents which may be used are basic aqueous solutions, aqueous solutions in a water-miscible solvent such as alcohol or a mixed solution thereof. The mixture is preferably adjusted to pH 9–12, then eluted at room temperature or with heating to some extent or with stirring. The adsorbent is removed by conventional means such as filtration to complete the elution. Then, if necessary, means such as chromatography, ultrafiltration, dialysis using a reverse osmosis filtration, etc. or removal of the salt therefrom may be applied to prepare the physiologically active substance of the present invention in a purer state.

The silicon components contained in the physiologically active substances of the present invention are water-soluble silicic acids, water-soluble silicates, polymers of water-soluble silicic acids, polymers of water-soluble silicates, or mixtures thereof. For example, the silicon components may be present as one or more silicic acids such as orthosilicic acid, metasilicic acid, mesodisilicic acid, mesotrisilicic acid, mesotetrasilicic acid, etc. or one or more alkali salts (e.g. sodium and potassium salts) thereof. They may be present in the form of monomers or in a polymerized form. The physiologically active substance of the present invention contains 1–20 micrograms/rag (preferably 1.5–15 micrograms/mg) of the silicon components when calculated as silicon.

The following examples illustrate the method for manufacturing the physiologically active substances of the present invention and their pharmaceutical effectiveness. In the examples, all parts, percentages, ratios, and amounts are by weight and all temperatures are in ° C. unless otherwise indicated:

EXAMPLE 1

Skin of a healthy adult rabbit was inoculated with vaccinia virus to activate or stress the tissues. The activated skin was aseptically removed, finely cut, and water was added thereto. The mixture was ground using a homogenizer to prepare an emulsion. The emulsion was filtered with pressure, the resulting filtrate was adjusted to pH 5.0 with hydrochloric acid and heated at 100° C. with a steam flow. Proteins were removed by filtration, the filtrate was adjusted to pH 9.1 with sodium hydroxide, heated at 100° C. and filtered. The filtrate was adjusted to pH 4.1, stirred after adding 2% of activated charcoal and the mixture was filtered to obtain a filtrate and a first batch of recovered activated charcoal. To the filtrate was added 5.5% of activated charcoal and the mixture was stirred for two hours and filtered to obtain a second batch of recovered activated charcoal. The first batch of recovered activated charcoal was mixed with water, adjusted to pH 9.9 with sodium hydroxide, stirred at 60° C. for 1.5 hours and filtered. Water was then added to the first batch of activated charcoal and to the second batch of activated charcoal. The pH of each batch was then adjusted to pH 10.9 with sodium hydroxide, and each batch was stirred at 60° C. for 1.5 hours and then filtered. The resulting filtrates were combined, neutralized with hydrochloric acid, desalted using a reverse osmotic filter membrane (molecular weight: 100) and dried in vacuo. The yield from 1 kg of the activated skin was 3 g. The physiologically active substance prepared as such exhibited the following properties:

(1) Characteristic: an amorphous and hygroscopic powder with a pale yellowish brown color containing 2–10 micrograms/mg of silicon components which are calculated as silicon;

(2) Solubility: it is soluble in water, methanol and ethanol and is insoluble in benzene and ether;

(3) pH: 6.0–8.3;

(4) Ultraviolet absorptions: $\lambda_{max}$=265–275 nm;

(5) Color reactions: amino acids (positive to a ninhydrin reaction), sugars (positive to an orcinol-iron (III) chloride-hydrochloric acid method), phosphorus (positive to a molybdenum blue method), proteins (negative to a trichloroacetic acid method) and Zphenols (negative to a ferric chloride method).

EXAMPLE 2

L cells (sarcoma cells of mice) were hypodermically transplanted to C3H mice, vaccinia virus was inoculated on the same place after ten days. Five days later, the areas of tumor inflammation were excised. The excised tissue (100 g) was finely cut, a 70% glycerol solution buffered to pH 7.0 was added, and the tissue was ground down using a Waring blender. A freezing/melting operation was repeated on the ground tissue three times. The milky ground liquid was centrifuged at 2,000× g for one hour, and the precipitates were removed. The pH of the supernatant fluid was adjusted to pH 5.0, and the fluid was heated at 100° C. and filtered. The filtrate was adjusted to pH 9.0, heated at 100° C. again and filtered to remove the insoluble matter. After cooling, the filtrate was adjusted to pH 4.5, and passed through a column filled with an activated charcoal. The column was then washed with distilled water and eluted with N/25 aqueous ammonia. Neutralization and desalting were carried out in the same manner as in Example 1 followed by drying in vacuo whereupon a powdery product was obtained. The physiologically-active substance of the present invention prepared as such contained a somewhat large amount of silicic acids. The amount of silicic acids contained in 1 mg of the hygroscopic powder was 5–14 micrograms calculated as silicon.

EXAMPLE 3

Pharmacological actions of the physiologically-active substance of the present invention are:

Experiment 1. Inhibiting the production of plasma kailikrein:

The inhibitory action of the physiologically-active substance against the production of plasma kallikrein was measured according to a method described in Kiso to Rinsho, vol. 20, no. 17, pages 399–405 (1986).

Thus, a suspension of kaolin was added to normal human plasma diluted with a physiologically saline solution. A lima bean trypsin inhibitor was added thereto after a certain period to stop the kallikrein proclution reaction. Then the resulting kallikrein was determined by using a synthetic substrate (D-Pro-Phe-Arg-p-nitroaniline). The test substance was placed in the above system whereby the inhibitory action of the test substance against the production of kallikrein was determined.

An example of the results is shown in Table 1. In Table 1 the potency of the activity is given in terms of the concentration ($IC_{50}$) at which the production of the plasma kallikrein was inhibited to an extent of 50%:

TABLE 1

| Substance Tested | $IC_{50}$ (micrograms/ml) |
|---|---|
| The substance of this invention | 35 |
| Indomethacin | 370 |
| Ketoprofen | 400 |
| Ibuprofen | 700 |
| Pentazocine | 1,600 |

Experiment 2. Improving peripheral circulation disturbance:

As an index for the action of the substance of the present invention for improving an abnormal sensation, the action of improving the peripheral blood circulation disturbance by quinoform was measured. Thus, quinoform was intraperitoneally administered to rats for 27 days with gradually increasing doses to cause a peripheral circulation disturbance. Then the hind paws were dipped in water having a temperature of 5° C. for two minutes to provide a low temperature load. The progress in the recovery of the paw temperature was monitored using thermographical image analysis to evaluate the effectiveness of the substance in improvement of the peripheral circulation disturbance. The substance of the present invention was intravenously administered to the rats consecutively for seven days from the 21st day after the administration of quinoform.

An example of the results is given in Table 2:

TABLE 2

| | Average Skin Temperature of the Hind Paws (°C.) 15 Minutes after Releasing the Low Temperature Load |
|---|---|
| Non-treated group | 27.3 ± 0.8 |
| Control group (treated with quinoform) | 24.1 ± 0.3 |
| Groups treated with the substance of the invention | |
| 50 mg/kg | 25.7 ± 0.3 |
| 100 mg/kg | 26.2 ± 0.7 |

It is clear from the results of Table 1 that the physiologically active substance of the present invention exhibits an unexpectedly superior inhibitory action against the production of plasma kallikrein. As discussed above, the plasma kallikrein acts on a high-molecular-weight kininogen whereby bradykinin is liberated and produced. The bradykinin has been known as a mediator for inducing peripheral blood vessel dilations, pains, inflammations and allergic reactions. Thus, when production of the plasma kallikrein is inhibited, the liberation of bradykinin can be inhibited. Accordingly, the substance of the present invention exhibiting an excellent inhibitory action against plasma kallikrein production is very highly useful as a pharmaceutical such as, for example, an analgesic, antiinflammatory and antiallergic drug. Further, the pharmacological activity of the physiologically-active substance of the present invention was tested in various systems both in vitro and in vivo whereupon it was found that the substance of the present invention exhibits excellent pharmacological activities such as peripheral blood flow improvement, antiinflammatory action and antiallergic action.

The physiologically active substances of the present invention can be made into various pharmaceutical preparations by combining the substance with various pharmaceutical carriers or diluents by conventional means to obtain solid, semisolid, liquid or aerosol preparations for oral or parenteral use. In the formulation, the substance of the present invention may be used solely or together in pharmaceutically effective amounts with pharmaceutically effective amounts of other pharmaceutically active components for treating animals or humans.

In the case of injections, a solution or a suspension comprising the substance of the invention may be prepared using an aqueous or nonaqueous solvent such as distilled water for injections, physiologically saline solution, Ringer's solution, plant oil, synthetic fatty acid glycerides, higher fatty acid esters, propylene glycol, etc. followed by adjusting the pH and isotonization.

In the case of preparations for oral administration, the substance of the invention ,per se or a mixture of it with suitable additives such as fillers (e.g., lactose, mannitol, corn starch, crystalline cellulose, etc.) may be combined together with one or more binders (e.g. gum arabicum, corn starch, gelatin, etc.), one or more disintegrating agents (e.g. corn starch, potato starch, carmerose, carmerose calcium, etc.), one or more lubricants (e.g. talc, magnesium stearate, etc.), bulking agents, moisturizers, buffers, preservatives, perfumes and the like, and mixtures thereof, to give tablets, diluted powders, granules or capsules. Depending upon the state of the patient and the type of the disease, preparation forms which are appropriate for the treatment or therapy for the disease may be prepared. Exemplary of such preparation forms are suppositories, inhalating agents, aerosols, ointments, cataplasms, eye drops, etc.

What is claimed is:

1. A physiologically active substance which is extracted from an activated animal tissue comprising an amorphous and hygroscopic powder containing 1–20 micrograms/mg of at least one silicon component calculated as silicon, the powder being soluble in water, methanol and ethanol and being insoluble in benzene and ether, said powder having a pH of 6.0 to 8.3, and ultraviolet absorptions of $\lambda_{max}=$ 265–275 nm.

2. A substance as claimed in claim 1 wherein the color reactions of said powder are: a) positive for amino acids, sugars and phosphorus and b) negative for proteins and phenols.

3. A substance as claimed in claim 2 wherein said at least one silicon component comprises at least one member selected from the group consisting of water-soluble silicic acids, water-soluble silicates, polymers of water soluble silicic acids, and polymers of water soluble silicates.

4. A substance as claimed in claim 3 which contains 2 to 10 micrograms/mg of said at least one silicon component, calculated as silicon.

5. A substance as claimed in claim 3 which contains 5 to 14 micrograms/mg of said at least one silicon component, calculated as silicon.

6. A substance as claimed in claim 1 wherein said tissue is activated by inoculation with a virus.

7. A substance as claimed in claim 1 wherein said tissue is activated by inoculation with a tumor-cultured cell strain derived from human beings or other animals.

8. A substance as claimed in claim 1 wherein said activated tissue is a member selected from the group consisting of cultured tissues, cultured cells, and inflammatory tissues of human or animal origin which are injected with virus.

9. A pharmaceutical composition comprising a pharmaceutically effective amount of a physiologically active substance which is extracted from an activated animal tissue, said substance comprising an amorphous and hygroscopic powder containing 1–20 micrograms/mg of at least one silicon component calculated as silicon, the powder being soluble in water, methanol and ethanol and being insoluble in benzene and ether, said powder having a pH of 6.0 to 8.3, and ultraviolet absorptions of $\lambda_{max}=$265–275 nm, and a pharmaceutically acceptable carrier.

10. A pharmaceutical composition as claimed in claim 9 wherein said carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, carmerose calcium, talc, and magnesium stearate.

11. A pharmaceutical composition as claimed in claim 9 which is a solid or semi-solid.

12. A pharmaceutical composition as claimed in claim 9 which is an aerosol.

13. A pharmaceutical composition as claimed in claim 9 wherein said animal tissue is selected from the group consisting of human hemocytes and placentae, kidney, skin, lung, testes, muscle, adrenal gland, thyroid gland, brain, nerve cells, and hemocytes.

14. A composition as claimed in claim 9 wherein the color reactions of said extract are: a) positive for amino acids, sugars and phosphorus and b) negative for proteins and phenols.

15. A method for treating a patient afflicted with inflammation, pain or allergic disease comprising administering a pharmaceutically effective amount of a water-soluble extract from animal tissue or animal cells which have been inoculated with a virus or a tumor cultured cell strain to generate substances which inhibit the production of plasma kallikrein, said extract comprising 1 to 20 micrograms/mg of at least one silicon component calculated as silicon and having ultraviolet absorptions of $\lambda_{max}$=265–275 nm, wherein the color reactions of the extract are: a) positive for amino acids, sugars and phosphorus, and b) negative for proteins and phenols, and wherein said at least one silicon component comprises at least one member selected from the group consisting of water-soluble silicic acids, water-soluble silicates, polymers of water soluble silicic acids, and polymers of water soluble silicates and wherein said water-soluble extract is admixed with a pharmaceutically acceptable carrier.

16. A method for treating a patient afflicted with inflammation, pain or allergic disease comprising administering a pharmaceutically effective amount of a water-soluble extract from an activated animal tissue, said extract comprising 1 to 20 micrograms/mg of at least one silicon component calculated as silicon and having ultraviolet absorptions of $\lambda_{max}$=265–275 nm, wherein the color reactions of the extract are: a) positive for amino acids, sugars and phosphorus, and b) negative for proteins and phenols and wherein said water-soluble extract is admixed with a pharmaceutically acceptable carrier.

17. A method as claimed in claim 16 wherein said carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, camerose calcium, talc, and magnesium stearate.

* * * * *